(12) United States Patent
Skerl et al.

(10) Patent No.: US 9,427,176 B2
(45) Date of Patent: Aug. 30, 2016

(54) IMPLANTABLE MEDICAL DEVICE

(75) Inventors: Olaf Skerl, Bad Doberan (DE);
Michael Lippert, Ansbach (DE); Jens Kirchner, Erlangen (DE)

(73) Assignee: BIOTRONIK SE & Co. KG (DE)

( * ) Notice: Subject to any disclaimer, the term of this patent is extended or adjusted under 35 U.S.C. 154(b) by 1018 days.

(21) Appl. No.: 13/227,522

(22) Filed: Sep. 8, 2011

(65) Prior Publication Data
US 2012/0245476 A1 Sep. 27, 2012

Related U.S. Application Data

(60) Provisional application No. 61/387,022, filed on Sep. 28, 2010.

(51) Int. Cl.
| | | |
|---|---|---|
| A61B 5/103 | (2006.01) | |
| A61B 5/11 | (2006.01) | |
| A61B 5/00 | (2006.01) | |
| A61N 1/365 | (2006.01) | |
| A61N 1/368 | (2006.01) | |

(52) U.S. Cl.
CPC ............ *A61B 5/1102* (2013.01); *A61B 5/0006* (2013.01); *A61N 1/3682* (2013.01); *A61N 1/3684* (2013.01); *A61N 1/36571* (2013.01); *A61N 1/36578* (2013.01)

(58) Field of Classification Search
CPC ...... A61B 5/1102; A61B 5/029; A61B 5/02; A61B 5/0006; A61N 1/365; A61N 1/3684; A61B 1/36578; A61N 1/36578; A61N 1/3682; A61N 1/36571
USPC .......................... 600/302, 481–483, 500–509
See application file for complete search history.

(56) References Cited

U.S. PATENT DOCUMENTS

| | | |
|---|---|---|
| 5,836,987 A | 11/1998 | Baumann et al. |
| 6,978,184 B1 | 12/2005 | Marcus et al. |
| 7,139,609 B1 | 11/2006 | Min et al. |
| 7,395,114 B2 | 7/2008 | Czygan et al. |
| 7,585,279 B2 | 9/2009 | Carlson et al. |
| 7,660,632 B2 | 2/2010 | Kirby et al. |

(Continued)

FOREIGN PATENT DOCUMENTS

EP 1 762 270 3/2007

OTHER PUBLICATIONS

McKay, et al. "Sternal acceleration ballistocardiography and arterial pressure wave analysis to determine stroke volume" Clin Invest Med 22(1), 1999, pp. 4-14.*

(Continued)

*Primary Examiner* — Navin Natnithithadha
*Assistant Examiner* — Eric Messersmith
(74) *Attorney, Agent, or Firm* — Craig A. Fieschko, Esq.; DeWitt Ross & Stevens S.C.

(57) ABSTRACT

An implantable medical device includes an integrated or connectable implantable three-dimensional acceleration sensor, and a ballistocardiogram (BCG) capturing unit that is connected or connectable to the acceleration sensor. The BCG evaluation unit processes an acceleration signal provided by the acceleration sensor and derives a BCG from the 3D accelerometer output signal. A BCG evaluation unit is connected to the BCG capturing unit, and is designed to evaluate a BCG provided by the BCG capturing unit and supply an output signal representing stroke volume.

23 Claims, 5 Drawing Sheets

(56) References Cited

U.S. PATENT DOCUMENTS

| | | | |
|---|---|---|---|
| 7,702,389 | B2 | 4/2010 | Czygan et al. |
| 7,883,469 | B2 | 2/2011 | Lippert et al. |
| 2002/0173826 | A1 | 11/2002 | Lincoln et al. |
| 2008/0194975 | A1 | 8/2008 | MacQuarrie et al. |
| 2008/0243202 | A1 | 10/2008 | Patangay et al. |
| 2009/0138060 | A1 | 5/2009 | Doerr |
| 2010/0094147 | A1* | 4/2010 | Inan et al. .................... 600/500 |
| 2010/0210921 | A1* | 8/2010 | Park et al. .................... 600/301 |
| 2011/0251502 | A1* | 10/2011 | Friedrich et al. ............. 600/500 |
| 2012/0065524 | A1* | 3/2012 | Morren et al. ................ 600/484 |
| 2013/0109989 | A1* | 5/2013 | Busse et al. .................. 600/527 |

OTHER PUBLICATIONS

Starr, et al. "Studies on the estimation of cardiac output in man, and of abnormalities in cardiac function, from the heart's recoil and the blood's impacts; the ballistocardiogram." Aug. 1, 1939. Amer. J. Physiol., vol. 127, No. 1, pp. 1-28.*

Cathcart, et al., "Comparison of Cardiac Output Determined by the Ballistocardiography (Nickerson Apparatus) and by the Direct Fick Method," J Clin Invest. 1953 Jan; 32(1): 5-14.*

M. Etemadi, O. T. Ivan, R. M. Wiard, G. T. A. Kovacs, and L. Giovangrandi, "Non-invasive assessment of cardiac contractility on a weighing scale", IEEE EMBC 2009, pp. 6773-6776, 2009.

* cited by examiner

IMPLANTABLE MEDICAL DEVICE

CROSS-REFERENCE TO RELATED APPLICATIONS

This patent application claims the benefit of U.S. Provisional Patent Application No. 61/387,022, filed on Sep. 28, 2010, which is hereby incorporated by reference in its entirety.

FIELD OF THE INVENTION

The invention relates to an implantable medical device, such as an implantable cardiac pacemaker or heart monitor, which includes means for capturing a stroke volume of a heart.

BACKGROUND OF THE INVENTION

A variety of methods are known for determining or estimating the stroke volume, i.e., the pumping capacity of the heart. Dilution methods (primarily thermal ones) are most common. Thermal dilution methods are disadvantageous for use in implants owing to their high power consumption and the need to provide access from outside of the body for delivering a temperature pulse. Additionally, continuous measurements using dilution methods are subject to significant limitations. Methods based on measuring the blood flow are also known, but the arrays used for measuring the blood flow using implanted sensors are relatively technically complex, and/or have high power requirements to measure or process the sensor signals.

Further methods employ intracardiac or intrathoracic impedance signals for deriving parameters used as a measure of the stroke volume or the change thereof (as seen, for example, in U.S. Pat. No. 7,395,114, EP 1 762 270, and U.S. Pat. No. 7,702,389). In the impedance-based methods, the parameters are determined from conductivity changes, which are only indirectly associated with the stroke volume and which are influenced by other factors. For example, U.S. Pat. No. 7,395,114 derives a degree of the ventricular contraction from the intracardiac impedance, and uses it to draw a conclusion regarding the stroke volume.

Measures of stroke volumes can also be determined using echocardiography. For example, geometric changes of the left ventricle can be determined and used to derive a measure of the stroke volume. Furthermore, the blood flow in the aortic arch can be approximately measured using the Doppler effect and used to estimate the stroke volume. However, these methods are undesirably complex for use in implants.

Methods have also been developed wherein parameters associated with measured cardiac sounds, under certain assumptions, correlate with the stroke volume. Frequently, acceleration sensors are employed for recording the cardiac sounds.

In U.S. Pat. No. 7,139,609, the cardiac sounds are isolated from the signal of an acceleration sensor, such as by suitable filtration. Based on empirical relationships, these cardiac sounds, primarily the first heart sound S1, are used to derive parameters which, under certain conditions, are related to the stroke volume. The cardiac sounds are additionally analyzed is with respect to characteristics that indicate impaired heart valve function in order to perform limited corrections to the calculated parameter, if necessary. Furthermore, the intracardiac electrogram (IEGM) is used in the determination of the parameters, requiring an additional electrode. Since a variety of other factors influence the characteristics of the cardiac sounds, it is apparent that the determination of the parameters from the cardiac sounds and the relationship thereof with the stroke volume is not very reliable. A similar method is disclosed, for example, in U.S. Pat. No. 7,585,279, in which a measure of the stroke volume is likewise approximated based on the heart sound S1.

It is known that other components can also be isolated from the signals of an acceleration sensor by suitable signal processing. One of these components is referred to as the seismocardiogram (SCG), which represents the vibration signals created by the beating of the heart in the thorax. The SCG contains the acceleration signals created by the mechanical movement of the heart in the thorax perpendicular to the body axis. This too can be used to determine parameters which, under certain conditions, are approximately related to the stroke volume, for example, according to U.S. Pat. No. 6,978,184. However, this process assumes a defined and fixed relationship between the mechanical movement of the heart and the pumping capacity, which does not unconditionally apply, especially in the case of cardiac insufficiency.

SUMMARY OF THE INVENTION

The invention involves an alternative implantable medical device which includes means for capturing a stroke volume of a heart. The implantable medical device includes an integrated acceleration sensor, or can be connected to an implantable acceleration sensor. The acceleration sensor is connected or can be connected to a BCG capturing unit. The BCG capturing unit is designed to process an acceleration signal provided by the acceleration sensor, derive a ballistocardiogram (BCG) from the 3D accelerometer output signal, and output it to a BCG evaluation unit. The BCG evaluation unit is designed to evaluate a ballistocardiogram provided by the BCG capturing unit and supply an output signal that represents a particular stroke volume.

The invention involves the realization that a ballistocardiogram (BCG) is a signal component of the acceleration sensor which represents the acceleration signals parallel to the body axis. The acceleration component parallel to the body axis is largely caused by the "recoil" as blood is ejected. U.S. Pat. No. 7,660,632 addresses this known effect and employs it as an option for determining the heart rate so as to control an implantable neurostimulator, but does not further analyze the ballistocardiogram or establish any relationship to the stroke volume and cardiac insufficiency.

Advantageously, the ballistocardiogram (BCG) is directly generated by the ejection of blood from the heart, and therefore provides a direct measure of the pumping capacity of the heart. Thus, the BCG allows direct monitoring of the pumping capacity and the heart rate status.

The ballistocardiogram (BCG) represents the acceleration signal parallel to the body axis. This acceleration is caused to a significant degree by the "recoil" as blood is ejected from the left ventricle. Similarly to the electrocardiogram (ECG), it is divided into different waves, the most important ones being I, J, K, L, and M. Contrary to the ECG, which represents the electrical excitation of the heart, the BCG represents the hemodynamic effect of the ventricular contraction. The J-wave in the BCG is created when the blood, after opening of the aortic valve, is pushed out of the left ventricle into the aortic arch. The acceleration pulse of the outflowing blood (blood pulse) causes a corresponding counter pulse ("recoil") in the body (body pulse):

$$m_K \cdot a_K = M_B \cdot a_B$$

In addition to the body mass $m_K$, the size of the body pulse $a_K$ is directly dependent on the mass of the ejected blood $m_B$ and the acceleration $a_B$ thereof. Thus, measures of the volume (mass) of ejected blood and the contractility of the ventricle can be derived from the body pulse $a_K$. These measures can be used to determine a parameter which approximately correlates with the stroke volume. For example, in the literature, methods have already been described by which a measure of the stroke volume can be determined with the help of a modified people scale [M. Etemadi, O. T. ban, R. M. Wiard, G. T. A. Kovacs, and L. Giovangrandi, "Non-invasive assessment of cardiac contractility on a weighing scale", IEEE EMBC 2009, pp. 6773-6776, 2009]. Advantageously, the BCG is directly related to the pumping capacity of the heart.

Many implanted pacemakers/ICDs are already equipped with an acceleration sensor for detecting patient activity and adapting the heart rate accordingly. The invention can use the same acceleration sensor to determine the BCG, and a measure of the stroke volume and contractility, by adapting the signal processing step used in the sensor. However, it is more advantageous to use a 3-axis acceleration sensor.

Thus, a preferred version of the implanted medical device (IMD)—which can be, for example, a cardiac pacemaker, ICD, monitoring implant, pressure sensor implant or the like—includes a suitable multi-axis (and preferably 3-axis) acceleration sensor. The implantable medical device may additionally include electrodes for recording the electrical activity of the heart (ECG, IEGM), as well as further sensors (such as pressure sensors).

A 3-axis design for the acceleration sensor enables the spatial positions of the individual acceleration vectors to be determined. As a result, the invention can compensate for the orientation of the implantable medical device in the body, and the acceleration vectors perpendicular and parallel to the body axis can be determined separately.

The signals of the acceleration sensor are used to determine the acceleration component located parallel to the body axis. Using suitable methods, the ballistocardiogram is separated from the acceleration signal parallel to the body axis, for example by using suitable band pass filters which suppress the cardiac sounds and the bodily movement components. In order to improve the signal quality, the BCG signal can suitably be further processed, such as by synchronous averaging over multiple cardiac cycles or additional filtration to suppress noise components.

As a result, diagnostically relevant parameters can be determined from the BCG signal, such as: a measure of the stroke volume, for example, from the amplitude difference between the I-wave and J-wave, or the amplitude of the J-wave; a measure of the cardiac output (CO) from the measure of the stroke volume and the heart rate determined from the BCG, ECG, IEGM or other signal components of the acceleration sensor; a contractility measure of the left ventricle, for example from the rise of the J-wave of the BCG signal; measures of the electromechanical coupling by including the ECG/IEGM, for example the time interval between the R-wave peak in the ECG and the peak of the J-wave in the BCG (R-J interval); the respective temporal synchronization of the pressure signal for the actual ejection of blood (when including the pressure signal of an implanted pressure sensor); the body position of the patient, by evaluating the vectors of the BCG and the gravitation field; and/or the current position of the implant in the body based on the vector of the BCG (and possibly also of the vector of the respiratory acceleration), for example to align ultrasonic sensors or telemetry antennas.

With respect to the determination of the measure of the cardiac output, a device including a heart rate capturing unit is preferred, which is designed to determine a heart rate signal by capturing recurring waves in the ballistocardiogram. However, the heart rate signal can also be obtained in the known manner from an electrocardiogram by determining the frequency with which R-waves recur, for example. The cardiac output can be obtained by multiplying the heart rate with the stroke volume, and can accordingly be formed from the heart rate signal and the output signal of the BCG evaluation unit representing the stroke volume.

The implantable medical device preferably includes a telemetry unit, which allows wireless data communication with an external device (patient device), telemonitoring, communication with a service center, and/or similar functions. Accordingly, one or all of the desired parameters can be determined entirely or partially in the implantable medical device, in a patient device, or in a service center.

Trends and trend parameters can be derived from the parameters, and can be further processed to, for example: monitor the status of the cardiac insufficiency; achieve an integration in a predictive model for forecasting the development of the disease or the effects of the treatment; optimize and track treatment parameters, for example in cardiac pacemakers, ICD or CRT devices (in particular, to optimize and track atrioventricular (AV) delay and intraventricular (VV) delay); and/or support the monitoring of the effects or side effects of drugs, and optimize drug therapies.

As explained above, a preferred device includes an acceleration sensor designed to capture acceleration in three axes. It is preferably designed to output a corresponding 3D accelerometer output signal as an acceleration signal to the BCG capturing unit.

The BCG capturing unit is preferably designed to derive a ballistocardiogram (BCG) from the acceleration signal, with the BCG capturing unit determining the acceleration vector acting in the longitudinal body direction and evaluating the course thereof over time.

A particularly preferred implantable medical device has the BCG evaluation unit determine I-waves and J-waves in a ballistocardiogram provided by the BCG capturing unit, and form the output signal representing a particular stroke volume based on the amplitude difference of consecutive I-waves and J-waves.

The implantable medical device preferably includes a sensing unit which has an electrode connected thereto, or to which an electrode can be connected, for recording an electrocardiogram (ECG). An R-wave characterizing a particular ventricular contraction can be detected in the recorded ECG. The implantable medical device can include a control unit connected to the sensing unit and BCG evaluation unit, and which can determine a time difference between the time at which an R-wave occurs in the electrocardiogram and the time at which a J-wave associated with the R-wave occurs in the ballistocardiogram as the R-J interval.

Further preferred versions of the invention can be developed by combining features noted above with each other, and/or with features noted in the following discussion of exemplary versions of the invention.

BRIEF DESCRIPTION OF THE DRAWINGS

Exemplary versions of the invention will now be discussed with reference to the figures, which illustrate.

DETAILED DESCRIPTION OF EXEMPLARY VERSIONS OF THE INVENTION

Figure 1:
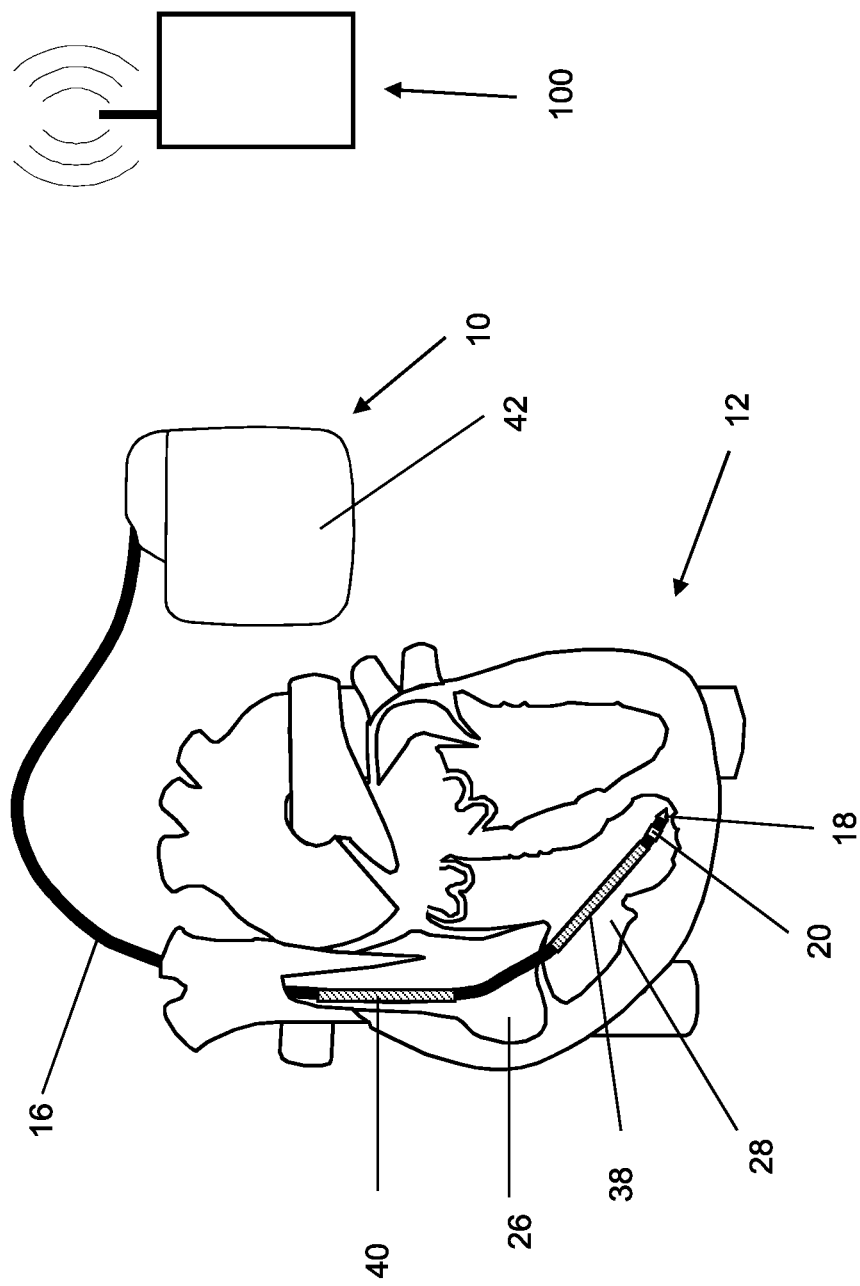
FIG. 1: a single-chamber cardioverter/defibrillator having a connected electrode lead.

FIG. 1 shows an implantable medical device 10 in the form of a single-chamber cardioverter/defibrillator (ICD) as a cardiac stimulator. Connected thereto is a single electrode lead, and specifically a right ventricular electrode lead 16. In the implanted state, the right ventricular electrode lead 16 ends in the right ventricle 28 of the heart 12.

At the distal end, the right ventricular electrode lead 16 carries a right ventricular tip electrode (RV Tip) 18 and slightly away therefrom a right ventricular ring electrode (RV Ring) 20. These electrodes are used to receive electric potentials in the right ventricle, and to deliver stimulation pulses to the right ventricle during normal pacemaker operation.

In addition, the right ventricular electrode lead 16 also carries a distal shock electrode (RV Coil) 38 and a proximal shock electrode (SVC coil) 40, which are used to deliver defibrillation shocks in the event of (true) ventricular fibrillation. The distal shock electrode (RV Coil) 38 is disposed in the right ventricle and the proximal shock electrode (SVC Coil) 40 is disposed in the superior vena cava (SVC).

Figure 2:
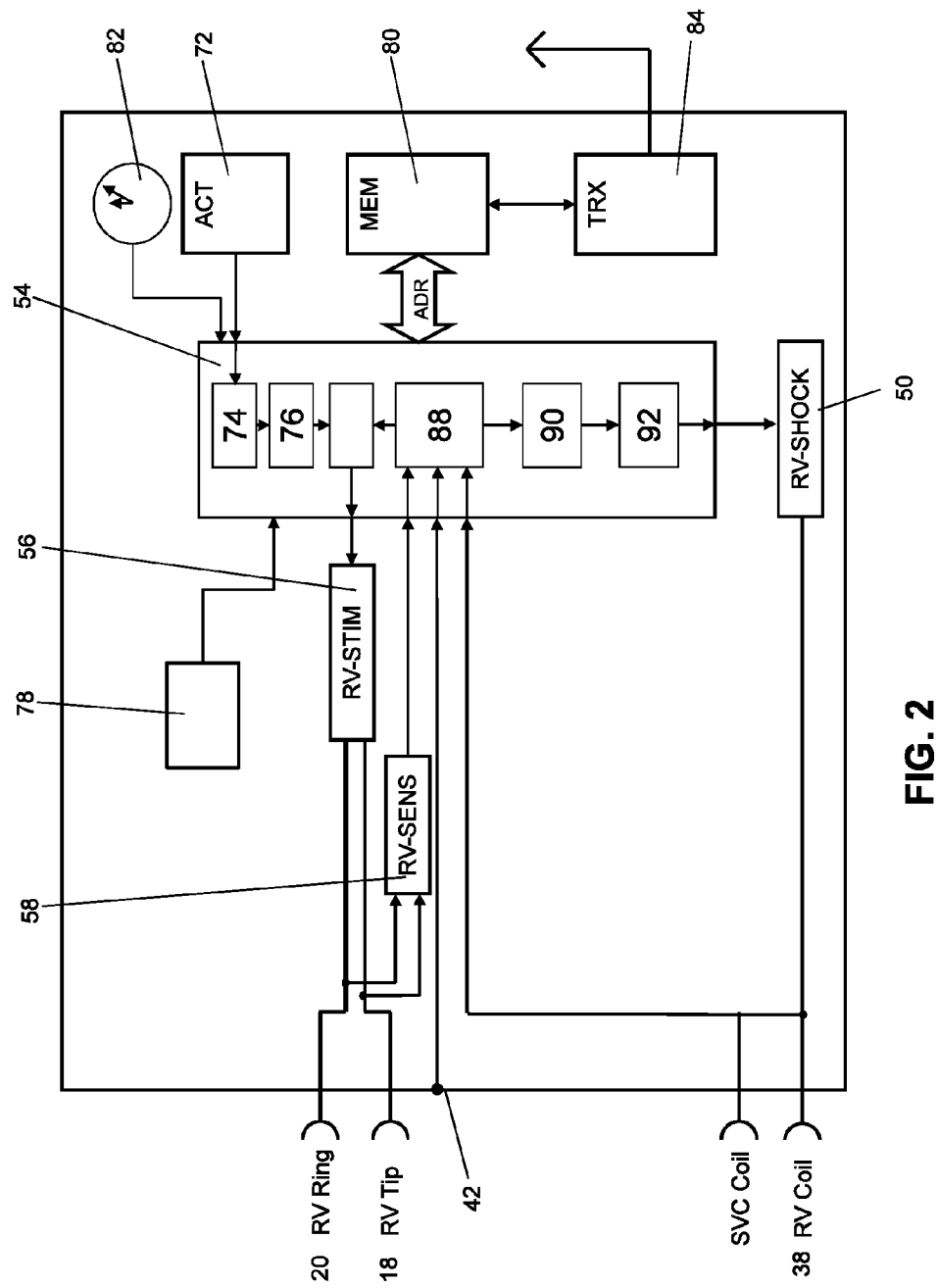
FIG. 2: a schematic block diagram of several components of the single-chamber cardioverter/defibrillator of FIG. 1.

FIG. 2 shows the main components of the cardiac stimulator 10 of FIG. 1. On the left side, the electrical connections for the different electrodes 18 (RV Tip), 20 (RV Ring), 38 (RV Coil), and 40 (SVC Coil) are shown. The shock electrodes 38 (RV Coil) and 40 (SVC Coil) are connected to a right ventricular shock pulse generator 50. The shock generator 50 is connected to a stimulation control unit 54, which controls the shock pulse generator 50 as needed for generating and delivering a defibrillation shock. In a preferred version, the shock generator 50 further includes a switching arrangement, not shown in detail in FIG. 2, by means of which either one or both shock electrodes 38 and 40 and/or the housing 42 are connected to the shock generator, so that the defibrillation shock can be delivered by way of an arbitrary combination of the shock electrodes 38 (RV Coil) and 40 (SVC Coil) and the housing 42.

The connection for the right ventricular tip electrode 18 (RV Tip) and the connection for the right ventricular ring electrode 20 (RV Ring) are in each connected both to a right ventricular stimulation unit 56 and to a right ventricular sensing unit 58. Both the right ventricular stimulation unit 56 and the right ventricular sensing unit 58 are connected to the control unit 54.

The right ventricular stimulation unit 56 is designed to generate a right ventricular stimulation pulse in response to an actuation signal from the control unit 54 and subsequently deliver it to the right ventricular ring electrode 20 (RV Ring) and the right ventricular tip electrode 18 (RV Tip). As an alternative, it is also possible for the housing 42 of the cardiac stimulator 10 to form a neutral electrode and for the right ventricular stimulation unit 56 to be connected to the connection for the right ventricular ring electrode 18 (RV Tip) and the housing 42 as another electrode for delivering a stimulation pulse. A right ventricular stimulation pulse differs from a defibrillation shock in that the stimulation pulse has significantly lower pulse intensity, so that unlike a defibrillation shock it does not excite the entire myocardium of a ventricle all at once, but only the myocardial cells in the direct vicinity of the right ventricular tip electrode 18 (RV Tip). This excitation then propagates over the entire right ventricle 28 as a result of natural stimulus conduction, thereby ensuring a stimulated contraction of the right ventricle 28.

The right ventricular sensing unit 58 is designed to first amplify the electrical potential present at the connection for the right ventricular ring electrode 20 (RV Ring) and the right ventricular tip electrode 18 (RV Tip) by way of an input amplifier, and to filter it. The right ventricular sensing unit 58 is further designed to evaluate the curves of the electrical signals present at the inputs thereof such that the right ventricular sensing unit 58 automatically detects a natural (intrinsic or automatic) contraction of the right ventricle 28. This can be done, for example, by comparing the curve of the signal present at the inputs of the right ventricular sensing unit 58 to a threshold value. Typically, the largest amplitude of the signal in the form of what is called the R-wave is characteristic of a natural contraction of the right ventricle 28, which can be detected by a comparison to a threshold value. The right ventricular sensing unit 58 then emits a corresponding output signal to the control unit 54, the signal indicating a natural contraction of the right ventricle 28.

In order to record intracardiac electrocardiograms, the control unit 54 includes an ECG capturing unit 88, which is connected both the housing 42 of the cardiac stimulator 10 as a first electrode and to the ventricular shock electrode (RV Coil) 38 as a second electrode. The electrocardiogram capturing unit 88 is additionally connected to the sensing unit 58. The sensing unit 58 generates a ventricular marker signal whenever it detects a ventricular event, as per the discussion above. The electrocardiogram capturing unit 88 utilizes this marker signal to detect a signal section containing a QRS complex in the recaptured electrocardiogram.

Similarly, one or more sensing units (not shown in FIG. 2) can be provided for the shock electrodes 38 (RV Coil) and 40 (SVC Coil). The sensing unit(s) is/are preferably designed to detect signals between the shock electrodes 38 (RV Coil) and 40 (SVC Coil), between the shock electrode 38 (RV Coil) and the housing 42, or between the shock electrode 40 (SVC Coil) and the housing 42. This is illustrated schematically in FIG. 2 by the connection of the shock electrodes 38 (RV Coil) and 40 (SVC Coil) as well as the housing 42 to the electrocardiogram (ECG) capturing unit 88.

As a further component of the cardiac stimulator 10, an acceleration sensor 72 is connected to the stimulation control unit 54 and integrated in the housing 42 of the cardiac stimulator 10. The acceleration sensor 72 is designed to capture a movement signal that is dependent on the physical activity of a patient and output a corresponding first accelerometer output signal to the control unit 54 that indicates the physical activity of the patient. This makes it possible for the stimulation control unit 54 to adapt the timing of the stimulation pulses to the (hemodynamic) needs of the patient.

The acceleration sensor 72 is designed to capture accelerations in three axes and output a corresponding 3D accelerometer output signal as an acceleration signal to the control unit 54. The control unit 54 includes a BCG capturing unit 74, which is designed to process the 3D accelerometer output signal and to derive a ballistocardiogram (BCG) from the signal, whereby the BCG capturing unit determines the acceleration vector acting in the longitudinal body direction and evaluates the course thereof over time.

A BCG evaluation unit 76 is connected to the BCG capturing unit 73, and is designed to evaluate a ballistocardiogram (BCG) provided by the BCG capturing unit 74 and supply an output signal representing a particular stroke volume. More particularly, the BCG evaluation unit 76 determines I-waves and J-waves in a ballistocardiogram provided by the BCG capturing unit and derives the output signal representing a particular stroke volume from the amplitude difference of consecutive I-waves and J-waves, or from the amplitude of the J-wave.

The control unit 54 is designed to determine a time difference between the time at which an R-wave occurs in the electrocardiogram—for example, represented by the corresponding marker signal—and the time at which a J-wave associated with the R-wave occurs in the ballistocardiogram (BCG), with this time difference defining the R-J interval.

In this way, the signals of the acceleration sensor can be used to determine the activity of the patient and his body position. The ballistocardiogram (BCG) can preferably be measured at times during which the patient is at rest and lying down in order to reduce the influence of body position and interference from body movements.

The acceleration sensor can be located in or on the housing of the implanted medical device to (as shown in FIG. 2), or can be separate therefrom and connected, for example, to the IMD by a cable.

Furthermore, the cardiac stimulator 10 includes a memory unit 80 which is connected to the control unit 54, and which allows it to store signals generated or evaluated by the control unit 54. The memory unit 80 also makes it possible to store control programs for the control unit 54 in modifiable form. The control unit 54 is also connected to a timer 82.

The memory unit 80 is connected to a telemetry unit 84, which makes it possible to wirelessly transmit data stored in the memory unit 80 to the external device 100, or to transmit programming commands from the external device 100 to the cardiac stimulator 10 and store them in the memory unit 80.

In particular, the telemetry unit 84 makes it possible to transmit data captured by the cardiac stimulator 10, including a particular ballistocardiogram (BCG) or variables derived therefrom, together with currently applicable treatment parameters via an external device 100 to a central service center, where the data can be further evaluated, and optionally, optimized treatment parameters can be determined. Further details are provided below.

Another optional feature of the cardiac stimulator 10 is a pressure sensor 78 for capturing an intracardiac pressure, with the sensor 78 being likewise connected to the control unit 54.

Figure 3:
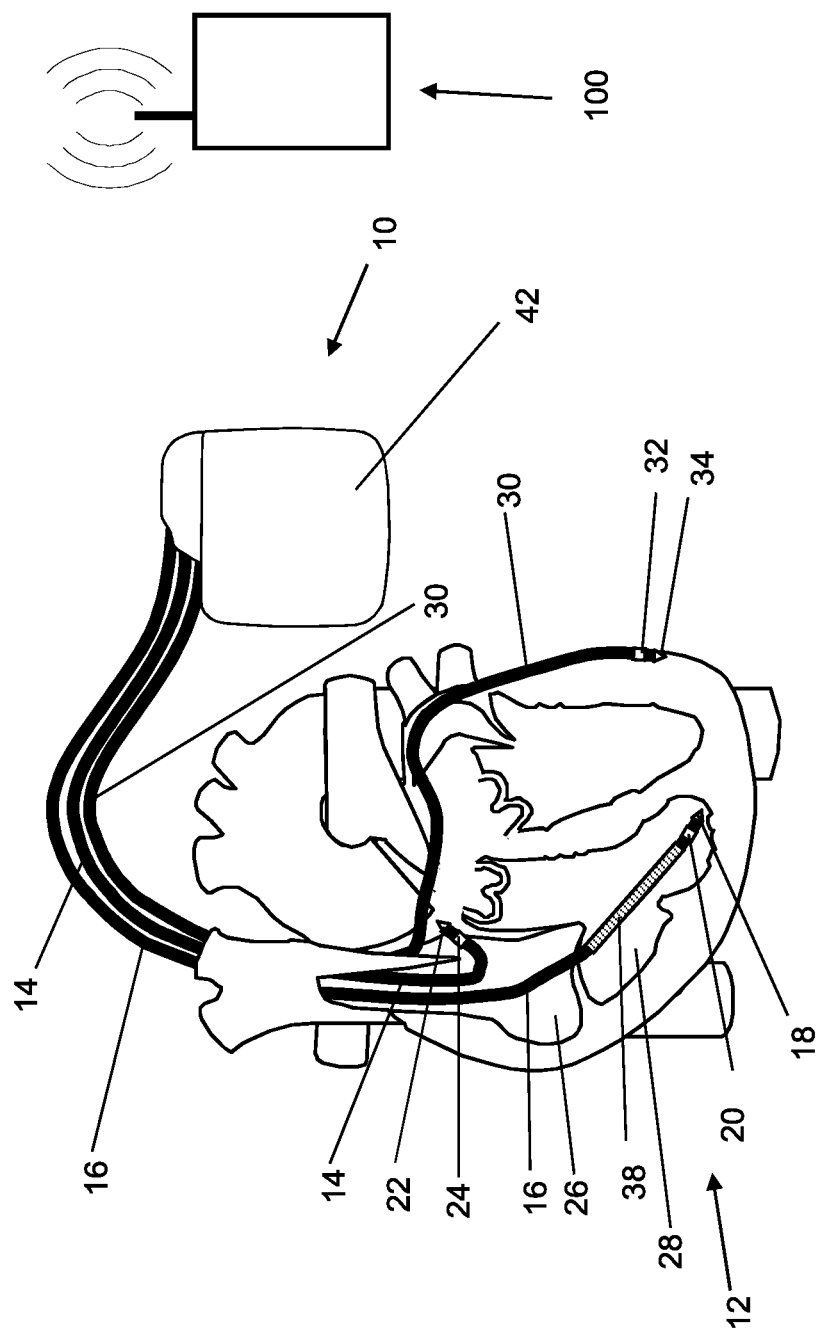
FIG. 3: a three-chamber cardioverter/defibrillator having connected electrode leads.

FIG. 3 shows an implant in the form of a biventricular three-chamber cardiac pacemaker and cardioverter/defibrillator (ICD) 10, which can be used as a CRT implant for cardiac resynchronization therapy (CRT). Connected to the implant 10 are three electrode leads, these being a right atrial electrode lead 14, a right ventricular electrode lead 16, and a left ventricular electrode lead 30. In the implanted state, the right atrial electrode lead 14 ends in the right atrium 26 of a heart 12. The right ventricular electrode lead 16 ends in the right ventricle 28 of the heart 12, and the left ventricular electrode lead 30 extends over the coronary sinus of the heart 12 to the left ventricle of the heart.

At the distal end, the right atrial electrode lead 14 carries a right atrial tip electrode 22 (RA Tip), and a small distance therefrom a right atrial ring electrode 24 (RA Ring). Similarly, at the distal end, the right ventricular electrode lead 16 carries a right ventricular tip electrode 18 (RV Tip) and slightly away therefrom a right ventricular ring electrode 20 (RV Ring). A left ventricular tip electrode 34 (LV Tip) and slightly away therefrom a left ventricular ring electrode 32 (LV Ring) are also disposed at the distal end of the left ventricular electrode lead 30. These electrodes are used to receive electric potentials in the respective ventricles and deliver stimulation pulses to the respective ventricles during normal pacemaker operation in a conventional manner.

The right ventricular electrode lead 16 additionally carries a right ventricular shock coil 38 (RV Coil) that is disposed in the right ventricle in the implanted state as the defibrillation electrode.

Figure 4:
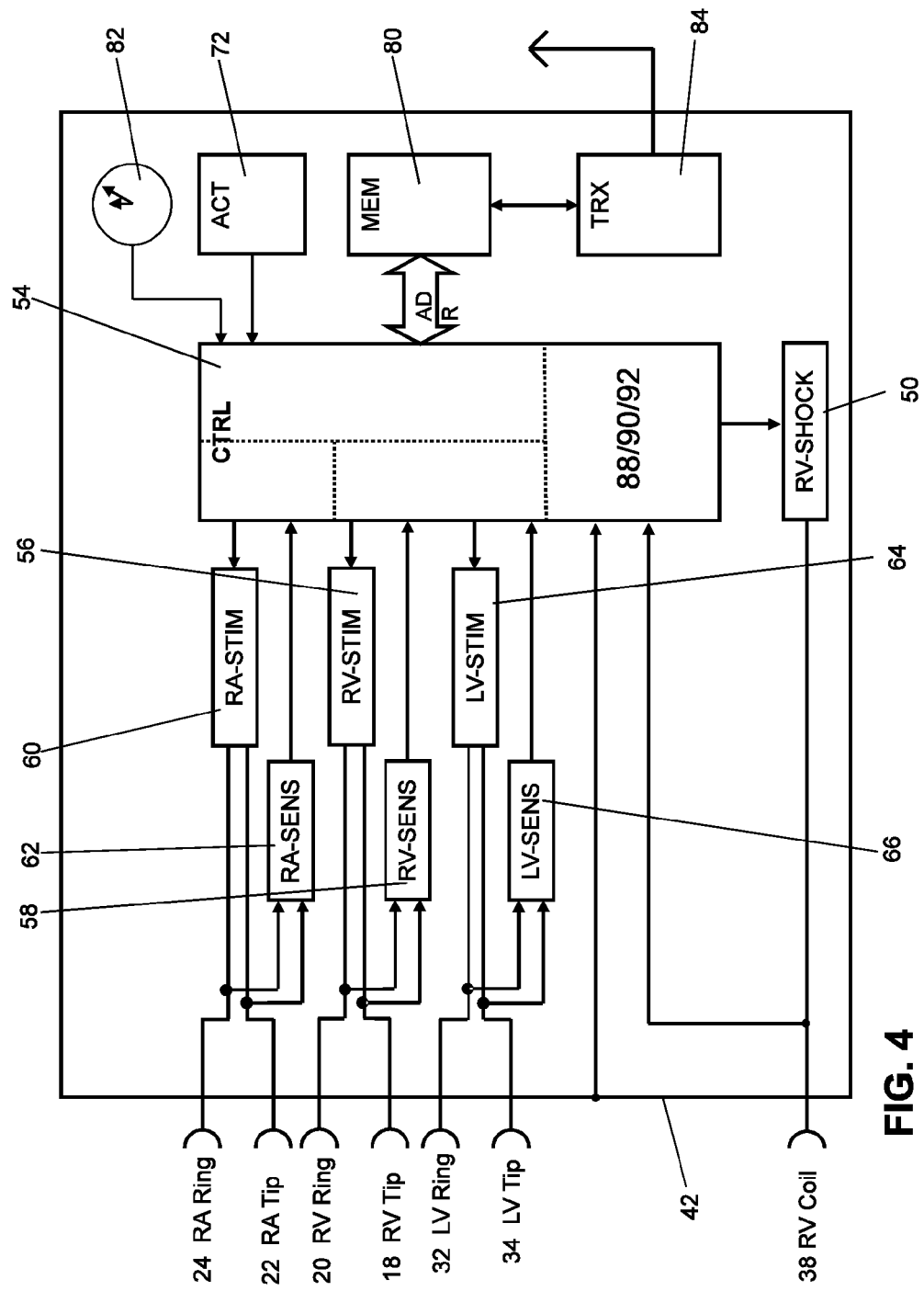
FIG. 4: a schematic block diagram of several components of the three-chamber cardioverter/defibrillator of FIG. 3.
Figure 5:
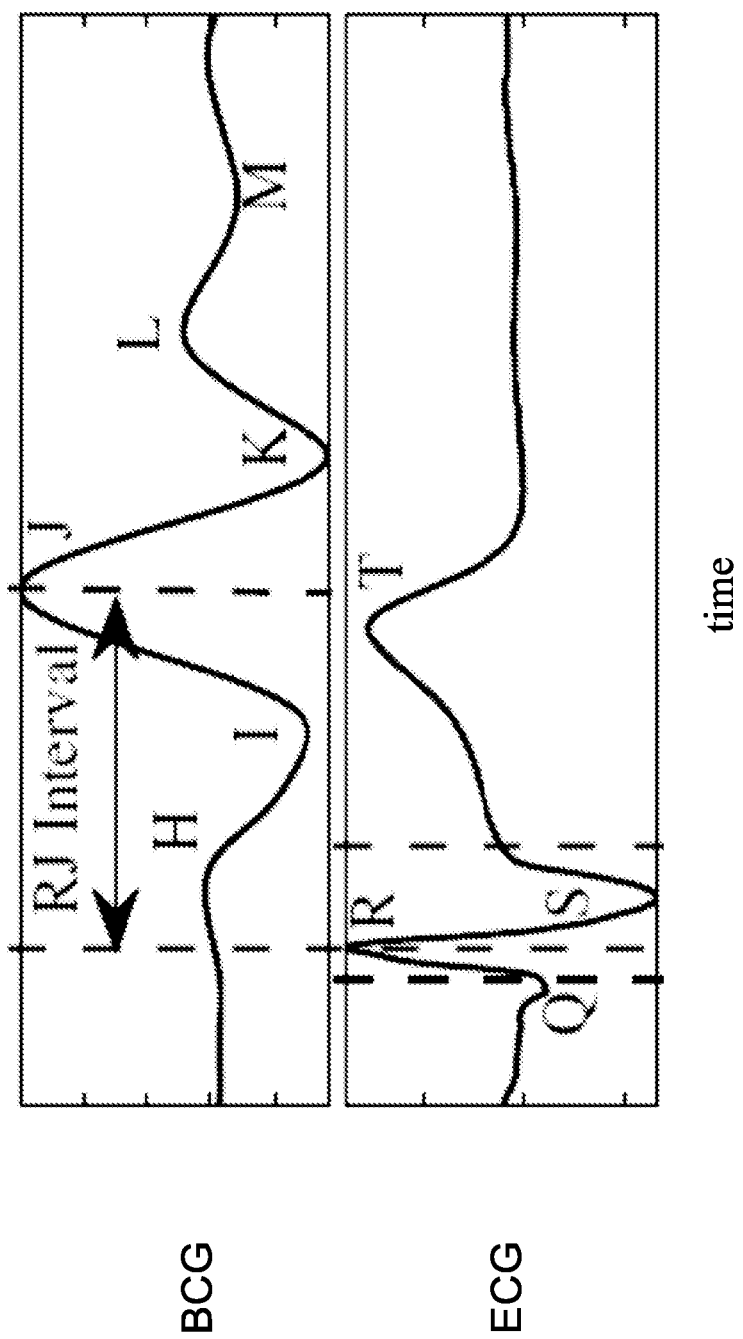
FIG. 5: relationships between ballistocardiogram, ECG, cardiac sounds and other variables associated with the cardiac cycle.

FIG. 4 shows the main components of the cardiac stimulator 10. Similarly to FIG. 2, on the left side the electrical connections for the different electrodes 18 (RV Tip), 20 (RV Ring), 22 (RA Tip), 24 (RA Ring), 32 (LV Ring), 34 (LV Tip), and 38 (RV Coil) are shown. The (only) shock electrode 38 (RV Coil) is connected to a right ventricular shock pulse generator 50.

The discussion provided above regarding the components of FIG. 2 and their operation applies as well to the right ventricular tip electrode RV Tip 18 and the right ventricular ring electrode RV Ring 20, the housing 42 (as a neutral electrode), the right ventricular stimulation unit 56, the right ventricular sensing unit 58, and the control unit 54.

Analogously, the right atrial tip electrode RA Tip 22 and the right atrial ring electrode RA Ring 24 are both connected to a right atrial stimulation unit 60 and to a right atrial sensing unit 62, which are each in turn connected to the control unit 54. The right atrial stimulation unit 60 is designed to generate stimulation pulses which are intense enough to excite the right atrial myocardium. The right atrial stimulation pulses can have different pulse intensities than the right ventricular stimulation pulses. The right atrial sensing unit 62 is designed to detect what is referred to as a P-wave from the curve of the differential signal present at the inputs, wherein the P-wave characterizes a natural (intrinsic) contraction of the right atrium 26. If the right atrial sensing unit 62 detects such a P-wave, it generates an output signal and passes it on to the control unit 54, characterizing a natural contraction of the right atrium 26.

Similarly, the left ventricular tip electrode LV Tip 34 and the left ventricular ring electrode LV Ring 32 are connected to a left ventricular stimulation unit 64 and to a left ventricular sensing unit 66. The left ventricular stimulation unit 64 and the left ventricular sensing unit 66 are likewise connected to the control unit 54. Both function similarly to the above-described stimulation units 56 and 60 and the sensing units 58 and 62.

Similarly, a sensing unit (not shown in FIG. 4) can be provided for the shock electrode (RV Coil) 38. This sensing unit is preferably designed to capture signals between the shock electrode (RV Coil) 38 and the housing 42. This is illustrated schematically in FIG. 4 by the connection of the shock electrode (RV Coil) 38 as well as the housing 42 to the ECG capturing unit 88.

The capture and evaluation of ballistocardiograms (BCGs) by appropriate implantable medical devices is discussed below, with two examples being given.

Example 1

An implantable medical device 10 (see FIG. 4) serving as a CRT implant contains a 3-axis acceleration sensor 72. The ballistocardiogram (BCG) is determined from the signals of the acceleration sensor 72 using the method discussed above. A measure for the stroke volume is determined from the ballistocardiogram, for example based on the amplitude difference between the I-wave and J-wave, and additionally the R-J interval is determined by way of the IEGM. Based on the R-J intervals and the measure for the stroke volume, the implantable medical device 10 automatically optimizes the treatment parameters and adapts them to the patient's physiological requirements. The measures for the stroke volume, the R-J intervals, and the treatment parameters set by the implantable medical device 10 are stored in the implantable medical device 10 and transmitted to a home monitoring service center via a telemetry connection. In the service center, trends are generated from the transmitted parameters and treatment parameters and they are processed as additional variables in a predictive model (predictor). The parameters and the treatment parameters can also be compared to threshold values in order to generate an alarm message where necessary.

Example 2

An implantable medical device designed as a monitoring implant is provided, and has no dedicated treatment function, thought it has sensors such as a 3-axis acceleration sensor and a sensor for ECG detection. The acceleration sensor's output is used to determine the ballistocardiogram (BCG) using the methods described above, as well as determining patient activity. A measure for the stroke volume is determined from the ballistocardiogram, for example from the amplitude of the J-wave, and is transmitted together with the other sensor values to an external device (patient device) and to a home monitoring service center via a telemetry connection. In the home monitoring service center, the stroke volume is included in the assessment of the state of health of the patient. In addition, the effects of treatment (such as medication) can be monitored, and the treatment can be adjusted if necessary.

Combination with Other Sensor Variables

The calculation and evaluation of the ballistocardiogram (BCG) can be supplemented with other sensor variables. These can serve, for example, as trigger signals for the cardiac cycle-synchronized averaging of the acceleration signal, or in order to allocate the characteristic computed from the ballistocardiogram to a defined physiological state, such as rest, activity, and the like.

At the same time, the characteristics determined from the ballistocardiogram (BCG), in particular time constants, can be used as additional information for the evaluation of other measured variables, such as for the impedance or blood pressure.

It will be apparent to those skilled in the art that numerous modifications and variations of the described examples and versions of the invention are possible in light of the foregoing discussion. The described examples and versions are presented for purposes of illustration only, and it is the intent to cover all such modifications and alternate versions that come within the scope of the claims below, or which are legally equivalent thereto.

What is claimed is:

1. An implantable medical device including:
    a. an acceleration sensor;
    b. a pressure sensor;
    c. a BCG capturing unit configured to:
        (1) receive an acceleration signal from the acceleration sensor, and
        (2) derive a ballistocardiogram from the acceleration signal; and
    d. a BCG evaluation unit configured to supply:
        (1) an output signal representing a stroke volume, the output signal being dependent on the ballistocardiogram, and
        (2) an output signal representing a contractility measure for a left ventricle from the ballistocardiogram, wherein the contractility measure is derived from the rise of a J-wave from the ballistocardiogram; and
    e. an evaluation unit configured to determine temporal synchronization of:
        (1) the pressure signal, and
        (2) blood ejection indicated by the ballistocardiogram.

2. The implantable medical device of claim 1 wherein the acceleration sensor is configured to:
    a. measure accelerations in three axes, and
    b. supply the accelerations to the BCG capturing unit as the acceleration signal.

3. The implantable medical device of claim 2 wherein the BCG capturing unit is configured to:
    a. determine from the acceleration signal an acceleration vector acting in the longitudinal direction of a body, and
    b. derive the ballistocardiogram from the acceleration vector.

4. The implantable medical device of claim 3 wherein the BCG evaluation unit is configured to evaluate:
    a. the acceleration vector acting in the longitudinal direction of a body, and
    b. a vertical direction from the acceleration signal, the vertical direction representing the direction of the gravitational field,
    and determine a patient body position therefrom.

5. The implantable medical device of claim 3 wherein the BCG evaluation unit is configured to evaluate:
    a. the acceleration vector acting in the longitudinal direction of a body, and
    b. a direction of a vector of respiratory acceleration,
    and determine a position of the implantable medical device in a body therefrom.

6. The implantable medical device of claim 1 wherein the BCG evaluation unit is configured to:
    a. determine I-waves and J-waves in the ballistocardiogram derived by the BCG capturing unit, and
    b. form the output signal representing the stroke volume based on the amplitude difference between consecutive I-waves and J-waves.

7. The implantable medical device of claim 1:
    a. further including a sensing unit configured to:
        (1) record an electrocardiogram (ECG) from an electrode, and
        (2) detect an R-wave characterizing a ventricular contraction in the recorded ECG,
    b. a control unit configured to determine an R-J interval, the R-J interval representing the time difference between:
        (1) the time at which an R-wave occurs in the electrocardiogram, and
        (2) the time at which a J-wave associated with the :R-wave occurs in the ballistocardiogram.

8. The implantable medical device of claim 1 further including:
    a. a heart rate capturing unit configured to supply a heart rate signal representing the heart rate, and
    b. a determination unit configured to generate an output signal representing a cardiac output based on:

(1) the heart rate signal, and
(2) the output signal representing the stroke volume.

9. The implantable medical device of claim 8 wherein the heart rate capturing unit is configured to determine the heart rate signal from recurring waves in the ballistocardiogram.

10. The implantable medical device of claim 1 wherein:
   a. the implantable medical device includes a telemetry unit configured for wireless data transmission, and
   b. the BCG evaluation unit is part of an external device in telemetric communication with the implantable medical device.

11. The implantable medical device of claim 1 wherein:
   a. the implantable medical device is defined by a biventricular cardiac stimulator for cardiac resynchronization therapy, and
   b. the BCG evaluation unit is connected to a treatment control unit for optimizing atrioventricular and/or intraventricular delay.

12. The implantable medical device of claim 1 wherein the implantable medical device is defined by a monitoring implant configured to lack any components for delivery of treatment to a body.

13. The implantable medical device of claim 1 further including:
   a, an electrode; and
   b. a treatment control unit configured to adapt electrical stimulation delivered by the electrode in dependence on the ballistocardiogram.

14. An implantable medical device including:
   a. a pressure sensor,
   b. an acceleration sensor,
   c. a BCG capturing unit configured to:
      (1) receive an acceleration signal from the acceleration sensor, and
      (2) derive a ballistocardiogram from the acceleration signal,
   d. a BCG evaluation unit configured to supply an output signal representing a stroke volume, the output signal being dependent on the ballistocardiogram, and
   e. an evaluation unit configured to determine temporal synchronization of:
      (1) the pressure signal, and
      (2) blood ejection indicated by the ballistocardiogram.

15. The implantable medical device of claim 14 further including:
   a. an electrode; and
   b. a treatment control unit configured to adapt electrical stimulation delivered by the electrode in dependence on the ballistocardiogram.

16. The implantable medical device of claim 14 wherein the BCG capturing unit is configured to:
   a. determine from the acceleration signal an acceleration vector acting in the longitudinal direction of a body, and
   b. derive the hallistocardiogram from the acceleration vector.

17. The implantable medical device of claim 14 wherein the BCG evaluation unit is configured to:
   a. determine I-waves and J-waves in the ballistocardiogram derived by the BCG capturing unit, and
   b. form the output signal representing the stroke volume based on the amplitude difference between consecutive I-waves and J-waves.

18. The implantable medical device of claim 14:
   a. further including a sensing unit configured to:
      (1) record an electrocardiogram (ECG) from an electrode, and
      (2) detect an R-wave characterizing a ventricular contraction in the recorded ECG,
   b. a control unit configured to determine an R-J interval, the R-J interval representing the time difference between:
      (1) the time at which an R-wave occurs in the electrocardiogram, and
      (2) the time at which a J-wave associated with the R-wave occurs in the ballistocardiogram.

19. The implantable medical device of claim 14 further including:
   a. a heart rate capturing unit configured to supply a heart rate signal representing the heart rate, and
   b. a determination unit configured to generate an output signal representing a cardiac output based on:
      (1) the heart rate signal, and
      (2) the output signal representing the stroke volume.

20. The implantable medical device of claim 14 wherein the BCC evaluation unit is configured to evaluate:
   a. the acceleration vector acting in the longitudinal direction of a body, and
   b. a direction of a vector of respiratory acceleration, and determine a position of the implantable medical device in a body therefrom.

21. The implantable medical device of claim 14 wherein the implantable medical device is defined by a biventricular cardiac stimulator for cardiac resynchronization therapy.

22. The implantable medical device of claim 21 further including a treatment control unit configured to optimize atrioventricular and/or intraventricular delay in dependence on parameters derived from the acceleration signal.

23. The implantable medical device of claim 14 wherein the implantable medical device is defined by a monitoring implant configured to lack any components for delivery of treatment to a body.

* * * * *